(12) United States Patent  
Skatter et al.

(10) Patent No.: US 7,548,606 B2
(45) Date of Patent: Jun. 16, 2009

(54) SYSTEM AND METHOD FOR INTEGRATING EXPLOSIVE DETECTION SYSTEMS

(75) Inventors: Sondre Skatter, Oakland, CA (US); Armin Uwe Schmiegel, Hamburg (DE)

(73) Assignee: GE Homeland Protection, Inc., Newark, CA (US)

( * ) Notice: Subject to any disclaimer, the term of this patent is extended or adjusted under 35 U.S.C. 154(b) by 196 days.

(21) Appl. No.: 11/469,095

(22) Filed: Aug. 31, 2006

(65) Prior Publication Data

US 2008/0056444 A1    Mar. 6, 2008

(51) Int. Cl.
*G01N 23/04* (2006.01)
(52) U.S. Cl. ............................................. 378/57; 378/4
(58) Field of Classification Search .................. 378/57, 378/4, 87, 205, 207
See application file for complete search history.

(56) References Cited

U.S. PATENT DOCUMENTS 5,367,552 A * 11/1994 Peschmann ................... 378/57
5,838,758 A * 11/1998 Krug et al. .................... 378/53
6,922,460 B2   7/2005 Skatter et al.
2005/0117700 A1* 6/2005 Peschmann ................... 378/57
2005/0123217 A1   6/2005 Schmiegel et al.
2005/0128069 A1* 6/2005 Skatter ....................... 340/522
2005/0169556 A1   8/2005 Schmiegel
2006/0078161 A1   4/2006 Schmiegel et al.
2006/0203960 A1* 9/2006 Schlomka et al. ............. 378/57

OTHER PUBLICATIONS

Bayesian inference, Wikipedia, The Free Encyclopedia, (http://en.wikipedia.org/wiki/Bayesian_inference).

* cited by examiner

*Primary Examiner*—Hoon Song
(74) *Attorney, Agent, or Firm*—Global Patent Operation

(57) ABSTRACT

An integrated detection system that includes a first threat detection apparatus and a second threat detection apparatus is provided. The first threat detection apparatus may identify one or more areas within an item of baggage that may contain threats. Example threats include, but are not limited to, explosives, weapons, illegal drugs, and hazardous matter, among others. The remaining areas are in theory deemed clear of threats. The second threat detection apparatus may be configured to inspect only the suspect areas of the item of baggage that was previously identified by the first threat detection apparatus. This improves throughput and lowers the false positive rate. A method for intelligently fusing the independent information obtained by the first and second threat detection apparatuses is also provided.

25 Claims, 5 Drawing Sheets

| | Threat Category 1 | Threat Category 2 | ... | Threat Category N | Clear |
|---|---|---|---|---|---|
| Person/Object 1 | 0.40 | 0.40 | ... | 0.00 | 0.20 |
| Person/Object 2 | 0.80 | 0.00 | ... | 0.10 | 0.10 |
| ... | ... | ... | ... | ... | ... |
| Person/Object M | 0.00 | 0.00 | ... | 0.10 | 0.90 |

FIG. 3

SYSTEM AND METHOD FOR INTEGRATING EXPLOSIVE DETECTION SYSTEMS

BACKGROUND

1. Field of the Invention

The technology disclosed herein generally relates to at least one apparatus and method for detecting targeted materials at security checkpoints or inline screening systems, and more particularly, to an apparatus and method for integrating first threat analysis data with second threat analysis data to provide an accurate and reliable final threat assessment.

2. Discussion of Related Art

With acts of global terrorism on the rise, detection of targeted materials has become increasingly important. Targeted materials may include, but are not limited to, explosives, weapons, and narcotics, among others. Advanced detection systems have been developed that can automatically identify not only the shapes of articles carried within baggage, but also the material characteristics and/or composition of those articles. Such detection systems include computed tomography (CT) scanners, quadropole resonance (QR) scanners, x-ray diffraction (XRD) scanners, and Advanced Technology (AT) scanners.

The performance of these detection systems is measured using three primary parameters, false positive rate, probability of detection, and scanning speed (throughput). Often, the improvement of one parameter occurs at the expense of another.

False positives occur when a detection system incorrectly identifies a harmless object/substance as an actual threat object/substance. False positives are commonly generated because conventional detection systems cannot always correctly distinguish actual threat objects/substances from harmless objects/substances in situations where both types of objects/substances exhibit similar threat characteristics, such as similar density and/or mass.

Detection systems are usually required to have a minimum probability of detection, or detection rate. The detection rate can be determined by systematically inserting objects containing one or more target materials of interest and then measuring the percentage of the times at which the detection system alarms.

Low numbers of false positives and high throughput are required for security checkpoints at public transportation facilities, such as airports. Co-pending U.S. patent application publication No. 2005/0128069 (hereinafter, "'069 publication"), describes how an upstream computed tomography (CT) scanner and a downstream quadropole resonance (QR) scanner, directly connected via a shared conveyor, may be used in sequence to reduce the number of false positives. The CT scanner scans an entire item of baggage and outputs a set of risk values indicative of the presence of particular types of targeted material. This risk values are inputted to the QR scanner, which scans the entire item of baggage a second time, generates its own risk values, and integrates these with the risk values inputted from the CT scanner.

Often, however, a second screening system will have considerable lower throughput than the first screening system. In such cases, it is desirable from a throughput point of view to screen only the part of the scannable object that contains the suspect region identified by the first system. Co-pending U.S. patent application publication No. 2005/0123217 (hereinafter, "'217 publication") describes a method for improving baggage throughput. The method determines whether and how an item of baggage's position has changed from one detection apparatus to the next, and saves time by permitting a downstream detection apparatus to examine only a particular suspect region within the item of baggage. This method is schematically represented in FIG. 5.

Referring to FIG. 5, a first threat detection apparatus takes a first transmission image 502. In the first transmission image 502, a first suspect region is identified, and a first list 518 of coordinates of the first suspect region is created. The item of baggage is then placed in a second threat detection apparatus, which takes a second transmission image 504 to determine the geometrical transformation between the coordinate systems of the two threat detection apparatuses. Each transmission images 502, 504 is subjected to pre-processing 506, 508, during which geometric rectification and optical pre-processing of intensities may be performed. Various features of the respective image contents are then measured in preparation for performing features extractions 510, 512. Comparative features are then determined and the second position of the scannable object relative to its first position is determined. The extracted features are appraised, and a calculation 514 of the change in position is performed. There is also a geometric transformation 516 of the images. Following the successful determination of position via the calculation 514 of the change of position, a second list 520 of coordinates of a transformed second suspect region is created. The coordinates of the second suspect region are the coordinates of the first suspect region that have been transformed into the second transmission image 504.

Thus, in the known integrated detection system described in the '217 publication, no intelligent fusion of the independent information obtained by the upstream detection apparatus and the downstream detection apparatus is performed. Additionally, the known threat detection system described in the '069 publication scans the entirety of an object multiple times. A need therefore exists for an improved integrated detection system that achieves high throughput with a minimal number of "false positives."

SUMMARY

The technology disclosed herein overcomes the disadvantages associated with the related art and meets the needs discussed above by providing an integrated detection system and a method for quickly, accurately, and reliably identifying whether particular types of targeted materials and/or targeted objects are present in scannable objects, including but not limited to, airline baggage.

In an embodiment, a method of detecting a type of threat in a scannable object may include the following steps, which may be performed in any suitable order. A step may include scanning a scannable object in its entirety in a first threat detection apparatus. Another step may include identifying, from an image of the scannable object, a suspect region in the scannable object. Another step may include scanning only the suspect region of the scannable object in a second threat detection apparatus. Another step may include combining and statistically processing preliminary risk value data generated by the first threat detection apparatus with present risk value data generated by the second threat detection apparatus. Another step may include outputting final risk value data indicative of a presence or absence of at least one of a targeted material and a targeted object in the suspect region.

In an embodiment, an integrated threat detection system may be provided that includes a first threat detection apparatus and a second threat detection apparatus. The first threat detection apparatus may be configured to: scan a scannable object in its entirety, identify a suspect region in an image of the scannable object, and generate preliminary risk value data. The second threat detection apparatus may be configured to scan only the suspect region of the scannable object. The second threat detection apparatus may be further configured to generate present risk value data based on said preliminary risk value data. The second threat detection apparatus may be further configured to combine and statistically process preliminary risk value data generated by the first threat detection apparatus with present risk value data generated by the second threat detection apparatus. The second threat detection apparatus may be further configured to output final risk value data indicative of a presence or absence of one of a targeted material and a targeted object in the suspect region.

In another embodiment, a method may begin by obtaining first threat analysis data from an entire scan of the scannable object by a first threat detection apparatus. The first threat analysis data may include preliminary risk value data. The preliminary risk value may include at least one of substance and first shape threat probability data for one or more threat categories. The method may further include the step of obtaining second threat analysis data from a scan of only a suspect region of the suspect object by the second threat detection apparatus. The second threat analysis data may include present risk value data that includes at least one of density and second shape threat probability data for the one or more threat categories. Another step may include combining and statistically processing at least the preliminary risk value data and the present risk value data using a Bayesian likelihood function. Another step may include outputting final risk value data. The final risk value data may include final threat probability data indicative of an actual presence or absence of the type of threat in the scannable object. The type of threat may be a particular type of targeted material and/or a particular type of targeted object.

Another embodiment of the invention may provide an apparatus configured to detect a threat in a scannable object. The apparatus may include an advanced technology (AT) scanner having dual-energy x-ray source/detector pairs. The AT scanner may be configured to obtain first threat analysis data from a scan of the entire scannable object. The first threat analysis data may include preliminary risk value data. The preliminary risk value data may include at least one of substance and first shape threat probability data for one or more threat categories.

The apparatus may also include a computed tomography (CT) scanner. The CT scanner may have at least one x-ray source/detector pair mounted to a rotatable gantry. The CT scanner may be configured to scan only a suspect region of the scannable object. Additionally, the CT scanner may be further configured to obtain second threat analysis data from a scan of only the second suspect region of the suspect object. The second threat analysis data may include present risk value data. The present risk value data may include at least one of density and second shape threat probability data for the one or more threat categories.

The CT scanner may be further configured to combine and statistically process at least the preliminary risk value data and the present risk value data using a Bayesian likelihood function, and to output final risk value data. The final risk value data may include final threat probability data indicative of an actual presence or absence of the type of threat in the scannable object.

BRIEF DESCRIPTION OF THE DRAWINGS

The above and other aspects of the various embodiments of the claimed invention will become more apparent when the following detailed description is considered together with the accompanying drawings in which:

FIG. 3 is a table illustrating an embodiment of threat probability data resulting from a scan of a scannable object;

DETAILED DESCRIPTION

Figure 1:
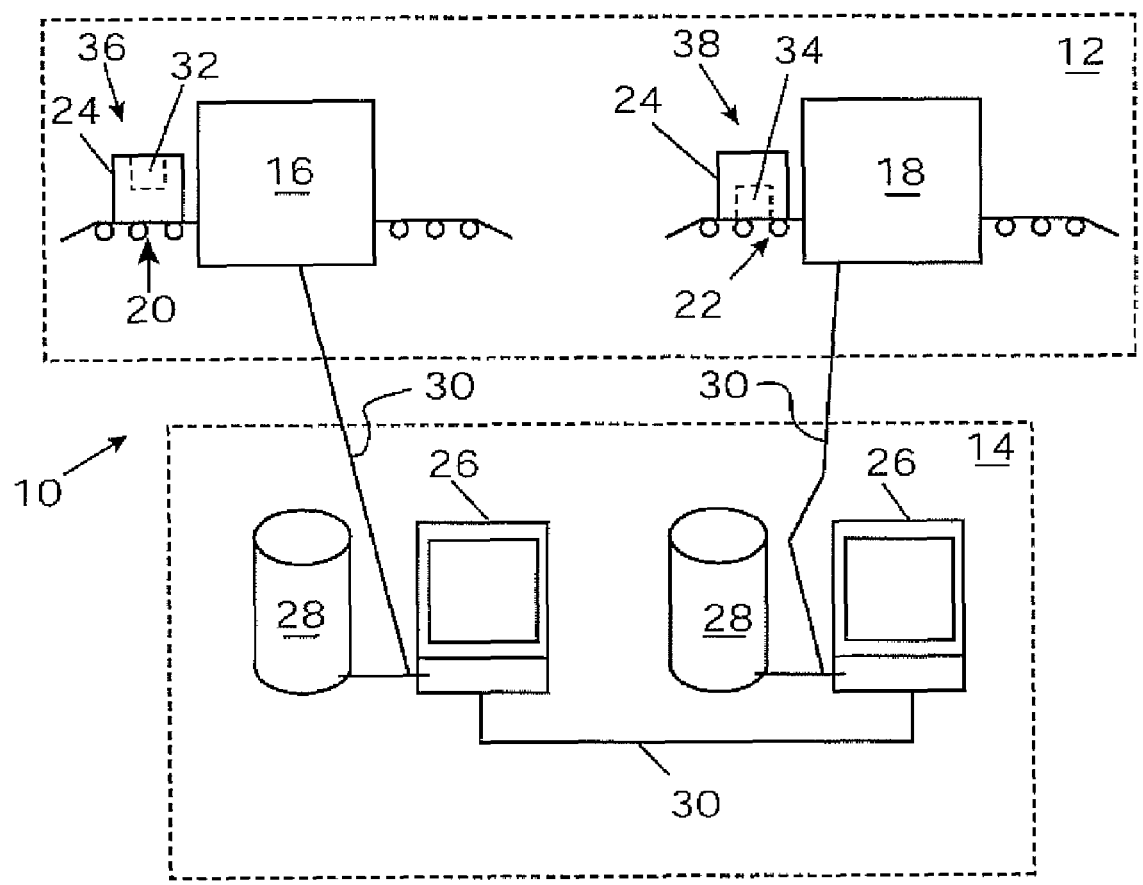
FIG. 1 is a schematic of an embodiment of an integrated detection system, including a scanning subsystem and a computer subsystem.

Reference is made herein to the accompanying drawings briefly described above, which show by way of illustration various embodiments of the claimed invention. Persons of ordinary skill in the above-referenced technological field will recognize that other embodiments may be utilized, and that structural, electrical, and procedural changes may be made without departing from the scope of the claimed invention. As used herein, the singular (illustratively, "region") includes the plural (illustratively, "regions"), and the plural includes the singular.

Embodiments of the invention described and claimed herein provide novel and non-obvious apparatus and methods for creating and operating integrated threat detection systems. In contrast to prior teachings that one performance parameter of an integrated threat detection system can only be improved at the expense of another performance parameter, embodiments of the claimed invention improve at least two performance parameters (throughput and false positive rate) simultaneously. These improvements may result, in part, from a unique data fusion among stage one, stage two, and/or stage three threat detection apparatuses.

In embodiments of the claimed invention, the dual energy x-ray information collected by a first threat detection apparatus enables inference of an effective atomic number of the threat. This is orthogonal data to density information collected by a second threat detection apparatus. A Bayesian data fusion of the information collected by the first threat detection apparatus and the density information collected by the second threat detection apparatus lowers overall false positive rates for the integrated threat detection system.

In one embodiment, the targeted screening of scannable objects is enabled by registration of x-ray images obtained from the two different types of threat detection apparatuses. First, a global registration may be performed, which computes the translational and rotational offsets of the scannable object as they appear in the two detection systems. Part of this global registration includes determining whether the scannable object has been flipped and/or rotated since being scanned by the first threat detection apparatus. Second, the target area identified by the first threat detection apparatus may be transformed into a target area in the second detection device by utilizing the image-offset parameters computed from the global registration. Thirdly, the x-ray attenuation in the two areas may be compared for verification. If they compare unfavorably, the target area of the second threat detection apparatus may be enlarged iteratively.

Independent data obtained by each of the first and second threat detection apparatuses may be transformed into threat probability evidence using likelihood functions and threat priors in a Bayesian probability theory framework. In one embodiment, a particular Bayesian framework (DSFP) for explosive detection may be employed. Other types of intelligent data fusion, however, are possible.

Advantages afforded by embodiments of the claimed invention include, but are not limited to: higher throughput for integrated threat detection systems; lower false positive rate; and fewer operators needed downstream from the second threat detection apparatus.

As a matter of convenience, one or more embodiments of the invention are described herein in the context of a baggage inspection system implemented as part of a typical airport security system. However, it is to be understood that the claimed invention is not so limited, and that many other applications are envisioned and possible within the teachings of the claimed invention. For example, applications of an integrated threat detection system constructed in accordance with the principles of the claimed invention include, but are not limited to, seaports, public buildings, public transportation facilities, prisons, hospitals, power plants, office buildings, hotels, casinos, and military facilities, among others.

The terms "baggage," "scannable object(s)," and "item of baggage," are used herein to generally refer to any type and size of an item, object, or substance that may be screened by an integrated threat detection system constructed in accordance with the principles of the invention, regardless of the size of the item/object and/or the quantity of the substance. Non-limiting examples of scannable objects may include suitcases, briefcases, backpacks, gels, liquids, gases, persons, cargo holds, over-the-road trailers, railcars, sea-land containers, and the like. The terms "baggage," "scannable object(s)," and "item of baggage," also include items/objects/substances that are contained within another item, object, and/or substance. Non-limiting examples may include boxes in a cargo hold, objects contained in carry-on or checked luggage, containers in a railcar that contain liquids or gases, and the like.

Many embodiments of an integrated threat detection system constructed in accordance with the principles of the invention may examine small-sized to medium-sized scannable objects, but others may examine large-sized scannable objects. Non-limiting examples of small-sized scannable objects are a personal digital assistant (PDA) and a digital music player, among others. Non-limiting examples of medium-sized objects are a suitcase and a backpack, among others. Non-limiting examples of a large-sized scannable object are semi-trailers, sea/land containers, automobiles, railroad cars, and aircraft, among others.

As used herein, the phrase "targeted material" includes both "targeted substances" and/or "targeted objects." A "targeted substance" may be any type of matter or substance for which detection is desired that can be identified by atomic number. Non-limiting examples include explosives, illegal drugs, hazardous matter (such as chemical/biological/nuclear substances), and the like. A "targeted object" may be any type of item for which detection is desired that can be identified at least by its cross-sectional shape and/or silhouette. Non-limiting examples of targeted objects include weapons such as firearms and knives, explosives such as ammunition, grenades, and pipe bombs; and drug paraphernalia such as hypodermic needles and glass pipes, among others. A "targeted object" may also include a "targeted material." As a non-limiting example, a firearm (targeted object) may contain metal, polymers, lubricants, and/or powder residue (e.g., targeted materials). Targeted objects may include organic materials and inorganic materials.

FIG. 1 is a schematic of an integrated threat detection system 10 that includes a scanning subsystem 12, and includes a computer subsystem 14 having that may include one or more databases 28.

The scanning subsystem 12 may include a first threat detection apparatus 16, a second threat detection apparatus 18, and conveyor belts 20, 22. As shown in FIG. 1, the outlet of the first threat detection apparatus 16 may be physically separated from the inlet of the second threat detection apparatus 18. For example, the first threat detection apparatus 16 could be located across the room, or in a different room/building, from the second threat detection apparatus 18. A communication means 30, such as a wired network, a wireless network, or a transferable computer disk, connects the first threat detection apparatus 16 (and/or a first computer 26 associated therewith) to the second threat detection apparatus 18 (and/or a second computer 26 associated therewith).

The first threat detection apparatus 16 and the second threat detection apparatus 18 may be any combination of any type of scanning device that may be configured to detect a targeted material and/or a targeted object. Thus, although several embodiments are illustratively described herein with reference to x-ray based scanning devices, the scope of the claimed invention is not so limited, and may include other types of scanning devices.

In an embodiment, the first threat detection apparatus 16 is an advanced technology (AT) hardware scanner (hereinafter referred to as "AT scanner") of the type known to persons skilled in the threat detection art, such as, but not limited to, a dual-energy x-ray scanner. The second threat detection apparatus 18 is a computed tomography scanner (hereinafter referred to as "CT scanner) of the type known to persons skilled in the threat detection art. In another embodiment, the first threat detection apparatus 16 may be a CT scanner, and the second threat detection apparatus may be an AT scanner.

The AT scanner 16 includes a detection area into which scannable objects may be placed. The AT scanner 16 further includes two fixedly mounted x-ray source/detector pairs. Each x-ray source has a different voltage relative to the other, and both x-ray sources are positioned to interrogate, with x-ray radiation, a scannable object placed within the detection area.

CT scanner 18 includes a gantry support with a tubular detection area therethrough. A rotatable gantry may be mounted to the gantry support and configured to rotate an X-ray source and X-ray detector, secured to diametrically opposing sides of the movable gantry, about the tubular detection area. The CT scanner may be configured to perform a pre-scan and/or a detailed scan of a scannable object 24. In an embodiment where the CT scanner is configured only to perform the detailed scan, a third threat detection apparatus may be positioned between the AT scanner and the CT scanner and configured to perform the pre-scan. The third threat detection apparatus may be coupled with the computer subsystem 14. In an alternate embodiment, the CT scanner may be configured to perform a full volumetric scan, thereby eliminating the need for a pre-scan.

Referring again to FIG. 1, the computer subsystem 14 may include one or more computers 26 and may optionally include at least one database 28 configured to be accessed by each of the computers 26. The computers 26 are of the type known to persons skilled in the computer and/or threat detection arts. As shown in FIG. 1, the one or more computers 26 may include a first computer configured to communicate with the first threat detection apparatus 16, and a second computer configured to communicate with the second threat detection apparatus 18 and/or with the first computer. Each computer 26 may be configured to trigger an alarm to alert operators of the integrated threat detection system to a suspected or actual threat if a calculated threat probability meets a pre-determined threshold.

Each of the computers 26 includes a main bus to which are coupled a main memory, a processor, an alpha-numeric input device, a display device, and/or one or more of the following: a static memory, cursor control device, a drive unit including a machine-readable medium, a signal generation device, and a network interface device. One or both of the database 28 and the static memory may be components of the computer subsystem 14. The machine-readable medium may include a set of instructions, which may be transferred to the processor and the main memory through the main bus. Additionally, a wired or wireless communication means 30 links the computer subsystem 14 with at least the first threat detection apparatus 16, the second threat detection apparatus 18, and the database 28.

In another embodiment, the computer subsystem 14 may include a single central computer having the components described above. The central computer may be coupled with the database 28, the first threat detection apparatus 16, and the second threat detection apparatus 18.

Figure 2:
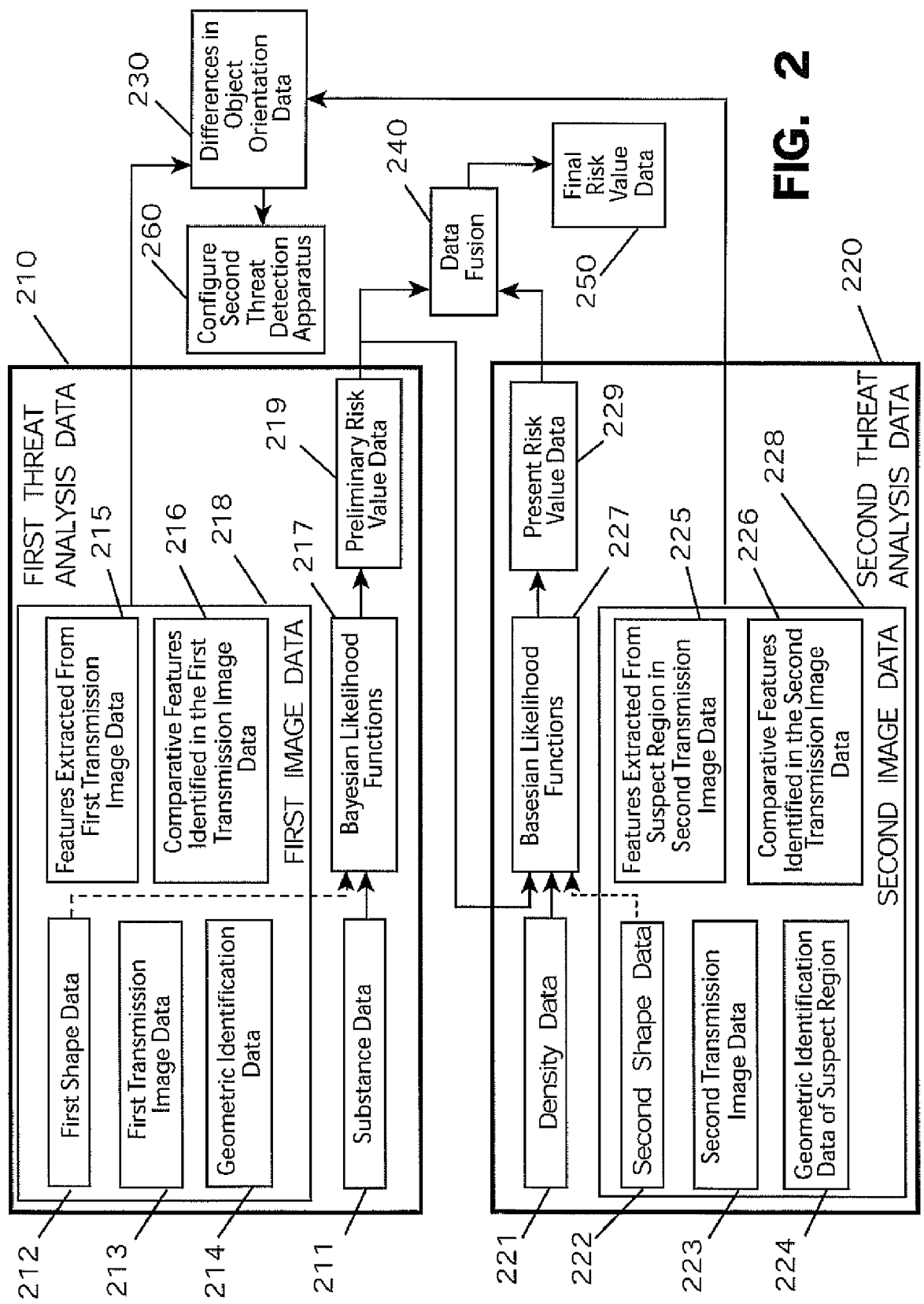
FIG. 2 is a flowchart illustrating an embodiment of a data fusion between first threat analysis data associated with a first threat detection apparatus and second threat analysis data associated with a second threat detection apparatus.

Referring to FIGS. 1 and 2, a technical effect afforded by embodiments of the invention may be a statistical data fusion 240 that outputs final risk value data 250. The data fusion 240 may combine and/or statistically process (in a Bayesian or other statistical framework) the preliminary risk value 219 and the present risk value data 229. The final risk value data 250 includes final threat probability data indicative of the presence or absences of a targeted material and/or a targeted object in the scannable object 24. The phrase "combine and statistically process" includes adding, subtracting, multiplying, dividing, comparing, averaging, generating and applying Bayes' rule, and/or otherwise processing first threat probability values included in the preliminary risk value data 219 together with second threat probability values included in the present risk value data 229.

In one embodiment, the first threat analysis data 210 associated with the first threat detection apparatus 16 may be stored in the database 28 and/or in the static memory, processed by the processor of at least the computer 26 coupled with the first threat detection apparatus 16, and/or inputted to the second threat detection apparatus 18. Similarly, the second threat analysis data 220 associated with the second threat detection apparatus 18 may be stored in the database 28 and/or in the static memory, and/or processed by the processor of the computer 26 coupled with the second threat detection apparatus 18. The final risk value data 250 may be stored in the database 28 and/or in the static memory. Any or all of the first threat analysis data 210, the second threat analysis data 220, differences in object orientation data 230, and final risk value data 230 may be displayed on a display device coupled with one or both the computers 26.

The first threat analysis data 210 may include, but is not limited to, substance data 211 indicative of a targeted substance detected within a first suspect region 32 of the scannable object 24; Bayesian likelihood functions 217; and preliminary risk value data 219 that includes substance and/or first shape threat probability data.

The first threat analysis data 210 may further include first image data 218. The first image data 218 may include, but is not limited to, first shape data 212 indicative of a targeted object detected within the first suspect region 32 of the scannable object 24; first transmission image data 213 showing the exterior, interior, and/or contents of the scannable object 24; geometric identification data 214 indicating the coordinates in the first transmission image data of the first suspect region 323; features 215 extracted from the first transmission image data 213; and comparative features 216 identified in the first transmission image data 213.

Similarly, second threat analysis data 220 may include, but is not limited to: density data 221 indicative of a targeted substance detected within a second suspect region 34 (that corresponds to the first suspect region 32 in a different orientation and/or coordinate system) of the scannable object 24; Bayesian likelihood function 227; and present risk value data 229 that includes density and/or second shape threat probability data. The second threat analysis data 220 may further include second image data 228. The second image data 228 may include, but is not limited to, second shape data 222 indicative of a targeted object detected within the second suspect region 34 of the scannable object 24; second transmission image data 223 showing at least an exterior, interior, or contents of the second suspect region 34; geometric identification data 224 indicating the coordinates of the second suspect region 34 in the second transmission image data 223; features 225 extracted from the second transmission image data 223; and comparative features 226 identified in the second transmission image data 223.

In one embodiment, the first image data 218 and the second image data 228 may be processed by a computer to obtain data 230 indicative of a difference (or differences) in the orientation of the scannable object 24 from one threat detection apparatus to another. The differences in object orientation data 230 may be used by the second threat detection apparatus 18 to translate the coordinates of the first suspect region 32 into the coordinates of the second suspect region 34. Once the coordinates of the second suspect region 34 have been determined, the second threat detection apparatus 18 may be configured 260 to scan and analyze only the second suspect region 34 to reduce scanning times and increase throughput.

In one embodiment, at least the preliminary risk value data 219 and the present risk value data 229 may be combined at data fusion 240 to generate final risk value data 250 indicative of the confirmed presence or absence of an actual threat in, or posed by, the scannable object 24. The final risk value data 250 may include, but is not limited to, final threat probability data, in one or more threat categories of interest, detected within the second suspect region 34 of the scannable object 24. The threat probability data may be, or may include, data identifying the type of targeted material and/or target object detected within the second suspect region 34.

In one embodiment, threat probability values may be calculated, using Bayesian likelihood functions 217 and 227 for each of the substance data 211 (and/or the first shape data 212) and the density data 221 (and/or the second shape data 222), respectively. The threat probability values may be used to trigger an alarm if one or more of the calculated probability values meets a predetermined critical probability value threshold. The preliminary risk value data 219 may include substance and/or first shape threat probability data values that indicate how likely the scannable object 24 is to contain a particular type of targeted material and/or a particular type of targeted object. In one embodiment, the present risk value data 229 may include density and/or second shape threat probability data values that indicate how likely the suspect region 34 is to contain the targeted material and/or the targeted object initially identified by the first threat detection apparatus 16.

FIG. 3 illustrates an exemplary threat probability data table 300 (hereinafter "table 300") that may be stored in the database 28 and/or the static memory. A separate threat probability table 300 may be created for each of the preliminary risk value data 219, the present risk value data 229, the data fusion 240, and the final risk value data 250. The table 300 may include "n" columns and "m" rows, where "n" is an integer greater than zero and where "m" is an integer equal to or greater than "n." As a non-limiting example, the table 300 illustratively shown in FIG. 3 includes four rows 310, 320, 330, 340, and five numbered columns 350, 360, 370, 380, 390. In FIG. 3, an unnumbered column filled with ellipsis " . . . " is illustratively positioned between columns 370 and 380, and an unnumbered row filled with ellipsis " . . . " is illustratively positioned between rows 330 and 340.

Row 310 may be a header row. The header row 310 may contain titles of various threat categories. Column 350 is illustratively titled "Person/Object." Column 360 is illustratively titled "Threat Category 1." Column 370 is illustratively titled "Threat Category 2." Column 380 is illustratively titled "Threat Category N," where "N" is an integer greater than two. Column 390 is illustratively titled "Clear." Each of rows 320, 330, and 340 may be data rows. In column 250, data row 320 may include data identifying a first scannable object (e.g., "Person/Object 1"); data row 330 may include data identifying a second scannable object (e.g., "Person/Object 2"); and data row 340 may include data identifying another scannable object (e.g., "Person/Object M"), where "M" is an integer greater than 2.

As shown in FIG. 3, threat probability data 301,302 is located at the intersections of one or more data threat category columns 360, 370, 380, and 390 and scannable object rows 320, 330, and 340. If the scannable object 24 is the first scannable object, its threat probability values are populated across row 320. If the scannable object 24 is the second or Mth scannable object, its threat probability values are populated across rows 330 and 340, respectively.

From FIG. 3, it can be seen that the threat probability values across each of rows 320, 330, and 340 total "1." Thus, each of the "preliminary risk values," "present risk values," and "final risk values" may be a number from 0 to 100, a percentage from 0% to 100%, or a number between 0 and 1, among other ranges.

The threat probability values in the table 300 signify the probability that a targeted object or targeted material is present in the scannable object 24. Thus, the threat probability values in row 320 may be interpreted as follows: "Person/Object 1" is 40% percent likely to contain: a) a first targeted material (and/or a first targeted object) associated with "Threat Category 1," and/or b) a second targeted material (and/or a second targeted object) associated with "Threat Category 2." Additionally, the "Person/Object 1" is 0% likely to contain an nth targeted material (and/or nth targeted object) associated with "Threat Category N." Consequently, "Person/Object 1" is 20% likely to be clear of targeted materials and/or targeted objects. Thus, in one embodiment, a low number in the "Clear" column 390 represents significant threat risk warranting further inspection and/or special handling of the scannable object 24, while a high number represents minimal threat risk that may not warrant further inspection and/or special handling of the scannable object 24. Illustratively, a non-limiting example of a low number in the "Clear" column 390 may be a value in the range of "0.00" to "0.59", while a non-limiting example of a high number may be a value in the range of "0.60 to 1.0."

A low number in any of "Threat Category" columns 360, 370, and 380 may indicate a minimal probability that a scannable object 24 contains a particular type of targeted material and/or a particular type of targeted object. Thus, referring again to table 300, the intersection of row 330 and column 380 contains a threat probability value of "0.1", which may signify that the scannable object 24 is 10% likely to contain a targeted material (and/or a targeted object) associated with the "Threat Category N." A high number in any of "Threat Category" columns 360, 370, and 380 may indicate a significant probability that a scannable object 24 contains a particular type of targeted material and/or a particular type of targeted object. Thus, referring again to table 300, the intersection of row 330 and column 360 contains a threat probability value of "0.8", which may signify that the scannable object 24 is 80% likely to contain a targeted material (and/or a targeted object) associated with the "Threat Category 1."

Referring to FIGS. 2 and 3, to populate a first table 300, first threat probability values are calculated by processing the substance data 211 (and/or the first shape data 212) with Bayesian likelihood functions 217. The first threat probability values collectively form the preliminary risk value data 219. To populate a second table 300, second threat probability values are calculated by processing the density data 221 (and/or the second shape data 222) with Bayesian likelihood functions 227. The first threat probability values may serve as priors for the Bayesian likelihood functions 227. The second threat probability values collectively form the present risk value data 229. To populate a third table 300, the first and second threat probability data (e.g., the preliminary and present risk value data 219,229) may be combined and/or statistically processed to generate final threat probability values, which collectively form the final risk value data 250. Depending on the value(s) of the final risk value data 250, an alarm may be triggered, and the scannable object 24 may be subjected to further scanning and/or special handling.

Figure 5:
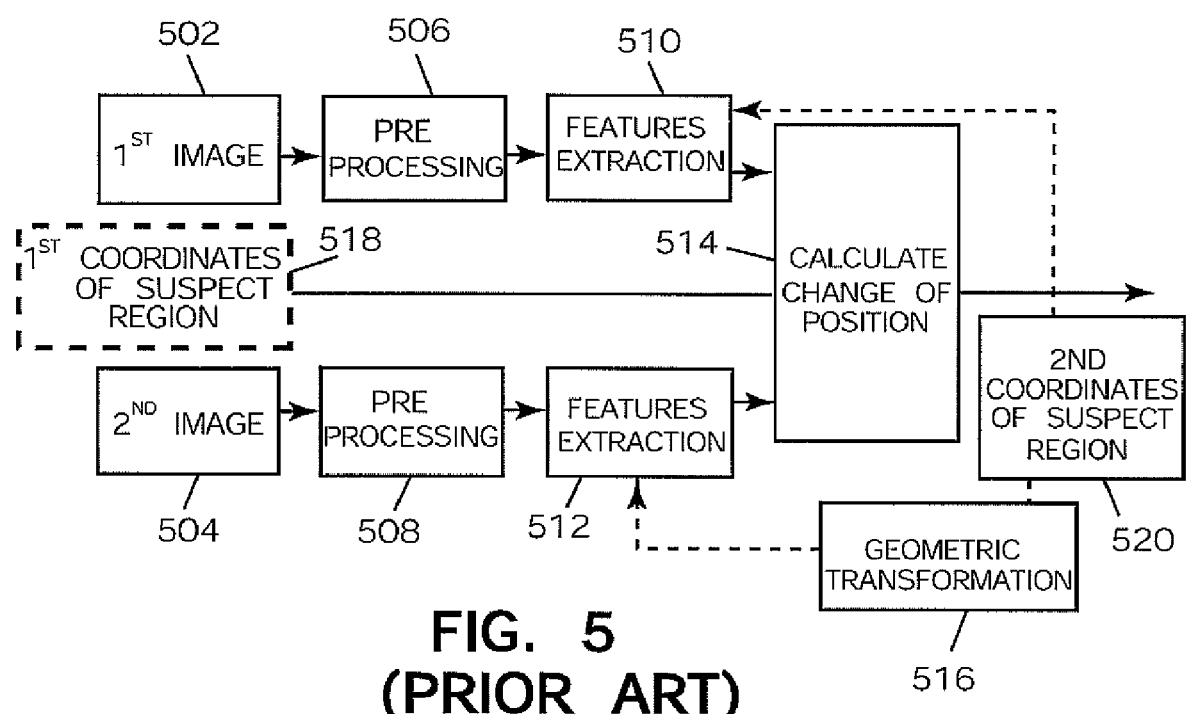
FIG. 5 is a flowchart illustrating a known method for comparing pictures of baggage, for determining a change in position of the baggage, and for determining a suspect region within the baggage.

An exemplary operation of the integrated threat detection system 10 is now described with reference to FIGS. 1, 2 and 3. To begin, a scannable object 24 may be placed in a first orientation 36 on a conveyor 20 within a passageway of a first threat detection apparatus 16, which in one embodiment, may be an AT scanner configured to produce x-rays of two different voltages. The two different x-ray voltages provided by the AT scanner create two different x-ray images of the scannable object 24 and provide dual-energy data indicative of the atomic number of one or more materials comprising and/or contained in and/or attached to the scannable object 24. The dual-energy x-ray data may be processed using conventional image processing techniques to form a first transmission image. The first transmission image may be used to determine the scannable object's first orientation 36 and/or to identify a first suspect region 32 within the scannable object 24. A list of coordinates of the first suspect region 32 may also be created, and various pre-processing steps (such as those described above with respect to FIG. 5) may be performed.

Once the dual-energy data identifies an atomic number, the atomic number may be correlated to a particular type of material associated with a predetermined threat category. For example, if an atomic number associated with cyclotrimethylenetrinitramine (RDX) (or other type of targeted material) is determined, a threat probability value, calculated using the Bayesian likelihood functions 217, may be entered into table 300 under a threat category 360, 370, or 380 to which RDX was previously associated, and a counterpart threat probability value may be entered into table 300 under the "Clear" column 390.

In like manner, any first shape data 212 identified by the CT scan data may be correlated to a particular type of targeted object previously associated with a predetermined threat category. The threat probability values associated with the first shape data 212 may be entered into the same or a different table 300 as the threat probability values associated with the density data 211.

When it is determined that a first suspect region 32 of a scanned object 24 contains (or is likely to contain) a targeted material and/or a targeted object, an alarm may trigger. Additionally, the preliminary risk value data 219 indicative of the same may be shared with the second threat detection apparatus 18 as Bayesian priors for the Bayesian likelihood functions 227. Additionally, the threat probability values associated with the first shape data 212 may be shared with the second threat detection apparatus 18 as Bayesian priors for the Bayesian likelihood functions 227. At data fusion 240, the preliminary risk value data 219 may be combined and/or statistically processed with the present risk value data 229 generated from the second threat detection apparatus 18.

Thereafter, the scannable object 24 may be positioned on a separate conveyor 22 for scanning and/or pre-scanning by the second threat detection apparatus 18, which may be a CT scanner having rotatable, gantry-mounted, x-ray source/detector pairs.

A second transmission image of the scannable object 24 may be used to determine whether the scannable object has been rotated and/or flipped (e.g., second orientation 38), and if so, what the coordinates of the first suspect region 32 are in the CT scanner's coordinate system. If differences in the object orientation 230 are determined, coordinates of a second suspect region 34 (which is the first suspect region 32 positioned within the CT scanner's coordinate system) are determined and used to configure the CT scanner to scan only the second suspect region 34. This reduces scan times and increases baggage throughput. The resulting x-ray CT image slices may be combined to create a three-dimensional view of the second suspect region 34 of the scannable object 24.

This three-dimensional view may be used to obtain density data 221 of the materials and/or second shape data 223 of the objects that comprise and/or are contained within the second suspect region 34.

Once the CT scan data identifies a material's density, the density value may be correlated to a particular type of targeted material associated with a predetermined threat category. For example, if a density associated with cyclotrimethylenetrinitramine (RDX) is determined, a threat probability value, calculated using the Bayesian likelihood functions 227, may be entered into a second table 300 under a threat category 360, 370, or 380 to which RDX was previously associated. Additionally, a counterpart threat probability value may be entered into the second table 300 under the "Clear" column 390.

In like manner, shape data identified by the CT scan data may be correlated to a particular type of targeted object associated with a predetermined threat category. The threat probability values associated with the second shape data 222 may be entered into the same or a different table 300 as the threat probability values associated with the density data 221.

At the data fusion step 240, the preliminary and present risk value data 219, 229 may, as previously described, be combined, and/or further processed using additional Bayesian likelihood functions to output final risk value data 250.

Figure 4:
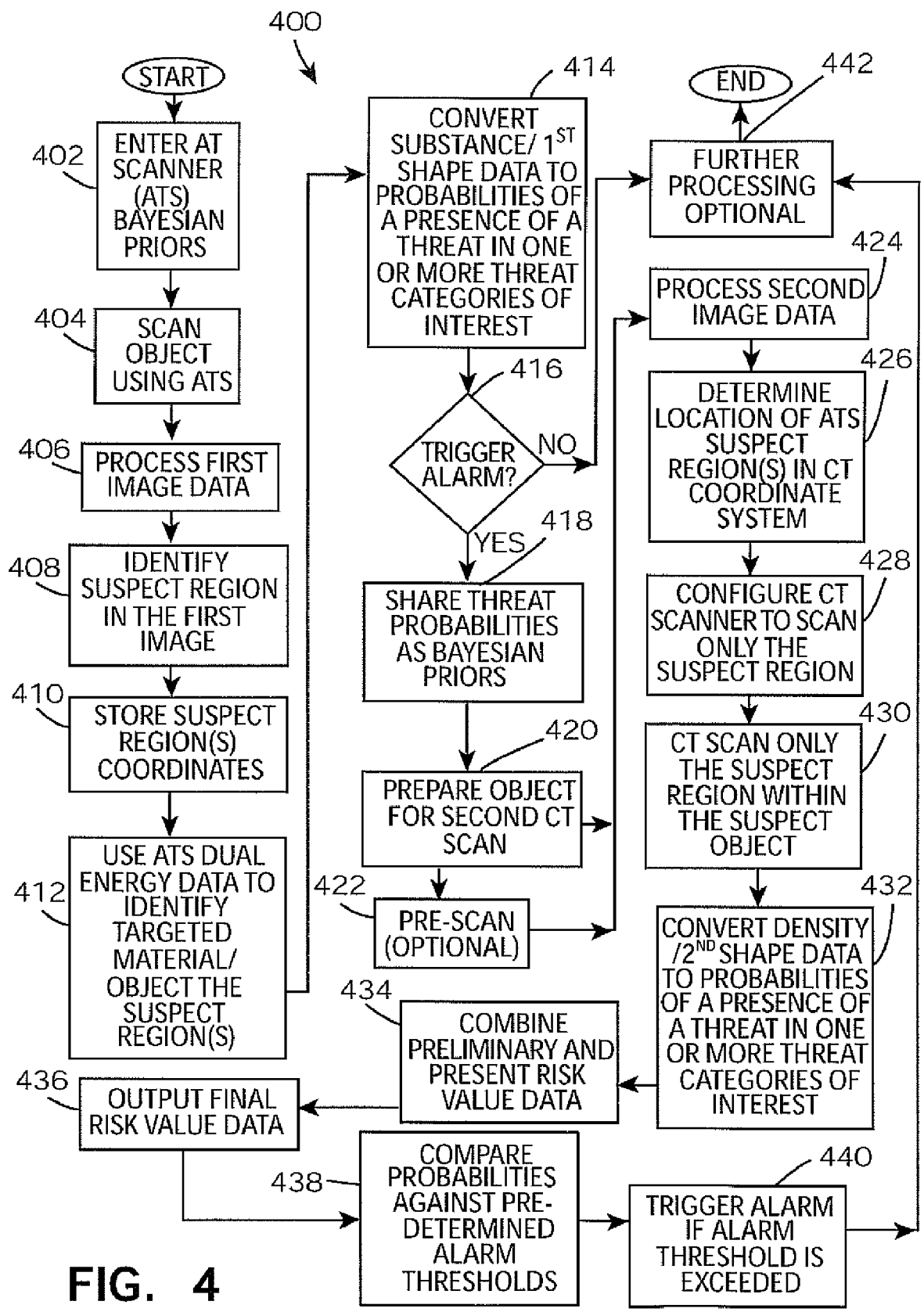
FIG. 4 is a flowchart illustrating an embodiment of a method of quickly, accurately, and reliably providing a final threat assessment of a suspect region within a scannable object.

FIG. 4 is a flowchart illustrating one embodiment of a method 400 of providing an accurate and reliable final threat assessment of a first suspect region 32 and a counterpart second suspect region 34 within a scannable object 24. The method 400 may begin at step 402 when initial Bayesian prior information is inputted to the computer associated with the AT scanner. The inputted Bayesian prior information may include pre-determined threat probability values associated with one or more types of scannable objects. For example, an exemplary prior substance threat probability value of "0.6" in a first threat category (such as "explosives") could be inputted for a scannable object such as a pistol case, whereas an exemplary prior threat probability value of "0.1" could be inputted in the same threat category for a different scannable object such as a handbag. Similarly, an exemplary prior shape threat probability value of "0.7" in a first threat category (such as "Firearm") could be inputted for a scannable object such as a person. Additionally, a pre-determined threat probability value may be inputted for a particular nationality of origin associated with the scannable object.

At step 404, the AT scanner scans the scannable object in its entirety and obtains both image data and substance data. At step 406, the image data is processed using any suitable image processing technique, and at step 408, a first suspect region in the scannable object is identified. Statistical analysis of the substance data may be used to identify and define the first suspect region, which is an area of the scannable object likely to contain a targeted material or targeted object. At step 420, the coordinates of the first suspect region are stored in a database and/or in a static memory. At step 412, the dual-energy x-ray data obtained from the AT scanner is processed to identify a probable targeted material and/or a targeted object in the first suspect region. At step 414, substance and/or first shape data obtained by the AT scanner is converted, using statistical analysis, into probabilities of a presence of a threat in one or more threat categories of interest, using one or more first Bayesian likelihood functions. At step 416, a decision is made. If a pre-determined threshold is not met, the scannable object may be subjected to optional further processing (step 438), such as a full scan by a subsequent scanner. If the pre-determined threshold is met, an alarm may be triggered. At step 418, if the alarm is triggered, the threat probabilities of step 414 may be shared with a second scanner as Bayesian priors.

At step 420, the scannable object is prepared for a second scan, which may be performed by a CT scanner. At step 422, and optional pre-scan may be performed to obtain second image data. At step 424, the second image data is processed using any suitable image processing technique. At step 426, differences in the orientation of the scannable object between scanning systems are determined, and the coordinates of the first suspect region are transformed into coordinates of a second suspect region. At step 428, the CT scanner is configured to scan only the second suspect region. At step 430, a CT scan of only the second suspect region is performed. At step 432, density and/or second shape data obtained by the CT scanner are converted to probabilities of a presence of a threat in one or more threat categories of interest, using one or more second Bayesian likelihood functions. At step 434, the preliminary and present risk data obtained from the AT scanner and the CT scanner, respectively, are combined as described above. At step 438, final risk value data is outputted and/or displayed on a display device. At step 440, the final threat probability values are compared with pre-determined thresholds. At step 442, an alarm is triggered if one or more of the alarm thresholds are met. At step 444, the scannable object may optionally be further processed. Thereafter, the method 400 may end.

A detailed description of various embodiments of the claimed invention has been provided; however, modifications within the scope of the claimed invention will be apparent to persons having ordinary skill in the above-referenced technological field. Such persons will appreciate that features described with respect to one embodiment may be applied to other embodiments. Thus, the scope of the claimed invention is to be properly construed with reference to the following claims.

What is claimed is:

1. A method of detecting a type of threat in a scannable object, the method comprising:
   scanning the scannable object in its entirety in a first threat detection apparatus;
   identifying, from an image of the scannable object, a suspect region in the scannable object;
   scanning only the suspect region of the scannable object in a second threat detection apparatus;
   combining and statistically processing preliminary risk value data generated by the first threat detection apparatus with present risk value data generated by the second threat detection apparatus; and
   outputting final risk value data indicative of a presence or absence of at least one of a targeted material and a targeted object in the suspect region.

2. The method of claim 1, wherein the first threat detection apparatus is an advanced technology scanner ("AT scanner"), and wherein the second threat detection apparatus is a computed tomography scanner ("CT scanner").

3. The method of claim 1, further comprising:
   storing coordinates of the suspect region; and
   configuring the second threat detection apparatus to scan only the suspect region of the scannable object.

4. The method of claim 1, further comprising:
   converting at least one of substance data and first shape data obtained by the first threat detection apparatus to first threat probability values for each of one or more threat categories of interest.

5. The method of claim 4, further comprising:
   converting at least one of density data and second shape data obtained by the second threat detection apparatus to second threat probability values for each of the one or more threat categories of interest.

6. The method of claim 1, wherein the scannable object is an item of baggage.

7. The method of claim 1, wherein the targeted material is one of an explosive, an illegal drug, and hazardous matter.

8. The method of claim 1, wherein the targeted object is a weapon.

9. An integrated threat detection system, comprising:
   a first threat detection apparatus configured to:
      scan a scannable object in its entirety,
      identify a suspect region in an image of the scannable object, and
      generate preliminary risk value data; and
   a second threat detection apparatus configured to:
      scan only the suspect region of the scannable object,
      generate present risk value data based on said preliminary risk value data,
      combine and statistically process preliminary risk value data generated by the first threat detection apparatus with present risk value data generated by the second threat detection apparatus, and
      output final risk value data indicative of a presence or absence of one of a targeted material and a targeted object in the suspect region.

10. The apparatus of claim 9, wherein the first threat detection apparatus is an advanced technology scanner ("AT scanner"), and wherein the second threat detection apparatus is a computed tomography scanner ("CT scanner").

11. The apparatus of claim 9, wherein the scannable object is an item of baggage.

12. The apparatus of claim 9, wherein the targeted material is one of an explosive, an illegal drug, and hazardous matter.

13. The apparatus of claim 9, wherein the targeted object is a weapon.

14. A method of detecting a type of threat in a scannable object, the method comprising the steps of:
   obtaining first threat analysis data from an entire scan of the scannable object by a first threat detection apparatus, wherein said first threat analysis data includes preliminary risk value data that includes at least one of substance and first shape threat probability data for one or more threat categories;
   obtaining second threat analysis data from a scan of only a suspect region of the suspect object by the second threat detection apparatus, wherein said second threat analysis data includes present risk value data that includes at least one of density and second shape threat probability data for the one or more threat categories;
   combining and statistically processing at least the preliminary risk value data and the present risk value data using a Bayesian likelihood function; and
   outputting final risk value data, wherein said final risk value data includes final threat probability data indicative of an actual presence or absence of the type of threat in the scannable object.

15. The method of claim 14, further comprising:
   determining coordinates of the suspect region in the scannable object;
   determining an offset in a scanning orientation of said scannable object between the first threat detection apparatus and a second threat detection apparatus; and
   configuring the second threat detection apparatus to scan only a second suspect region of the scannable object that corresponds to the first suspect region.

16. The method of claim 14, wherein the type of threat is one of a targeted material and a targeted object.

17. The method of claim 14, wherein the first threat detection apparatus is an AT scanner and wherein said second threat detection apparatus is a CT scanner.

18. The method of claim 14, wherein the step of outputting final risk value data further comprises at least one of:
   displaying the final risk value data on a display device; and
   triggering an alarm if a final threat probability value meets a predetermined threshold.

19. The method of claim 14, wherein the step of determining the offset in scanning orientation of the scannable object comprises:
   pre-scanning the entire scannable object.

20. The method of claim 14, wherein the scannable object is an item of baggage.

21. An apparatus configured to detect a threat in a scannable object, the apparatus comprising:
   an advanced technology (AT) scanner having dual-energy x-ray source/detector pairs,
      wherein the AT scanner is configured to obtain first threat analysis data from a scan of the entire scannable object, wherein said first threat analysis data includes preliminary risk value data that includes at least one of substance and first shape threat probability data for one or more threat categories; and
   a computed tomography (CT) scanner having at least one x-ray source/detector pair mounted to a rotatable gantry,
      wherein the CT scanner is further configured to scan only a suspect region of the scannable object, wherein the CT scanner is further configured to obtain second threat analysis data from a scan of only the second suspect region of the suspect object, wherein said second threat analysis data includes present risk value data that includes at least one of density and second shape threat probability data for the one or more threat categories, wherein the CT scanner is further configured to combine and statistically process at least the preliminary risk value data and the present risk value data using a Bayesian likelihood function, and wherein the CT scanner is further configured to output final risk value data that includes final threat probability data indicative of one of an actual presence and an absence of the type of threat in the scannable object.

22. The apparatus of claim 21, wherein the CT scanner is configured to determine an offset in a scanning orientation of said scannable object between the AT scanner and the CT scanner, and wherein the AT scanner is further configured to determine coordinates of the suspect region in the scannable object.

23. The apparatus of claim 21, wherein the scannable object is an item of baggage.

24. The apparatus of claim 21, wherein the targeted material is one of an explosive, and illegal drug, and hazardous matter.

25. The apparatus of claim 21, wherein the targeted object is a weapon.

* * * * *